(12) United States Patent
Ko et al.

(10) Patent No.: US 12,109,375 B2
(45) Date of Patent: Oct. 8, 2024

(54) REUSE PREVENTION SAFETY CATHETER

(71) Applicant: MEDIFIRST CO., LTD., Chungcheongnam-do (KR)

(72) Inventors: Kwon Cheul Ko, Sejong (KR); Chi Jeong An, Chungcheongnam-do (KR)

(73) Assignee: MEDIFIRST CO., LTD., Chungcheongnam-do (KR)

( * ) Notice: Subject to any disclaimer, the term of this patent is extended or adjusted under 35 U.S.C. 154(b) by 840 days.

(21) Appl. No.: 17/053,227

(22) PCT Filed: Sep. 30, 2019

(86) PCT No.: PCT/KR2019/012681
§ 371 (c)(1),
(2) Date: Nov. 5, 2020

(87) PCT Pub. No.: WO2021/010542
PCT Pub. Date: Jan. 21, 2021

(65) Prior Publication Data
US 2023/0095848 A1    Mar. 30, 2023

(30) Foreign Application Priority Data
Jul. 15, 2019    (KR) .......................... 10-2019-0085075

(51) Int. Cl.
*A61M 25/06*    (2006.01)
(52) U.S. Cl.
CPC ... *A61M 25/0631* (2013.01); *A61M 2205/273* (2013.01)
(58) Field of Classification Search
CPC ........ A61M 2205/273; A61M 25/0631; A61M 25/0612; A61M 25/06; A61M 25/0606; A61M 2005/1585; A61M 25/0097; A61M 5/50; A61M 25/0618; A61M 2025/0018; A61M 2025/0175; A61M 25/0625; A61M 2005/325; A61M 5/3273;
(Continued)

(56) References Cited

U.S. PATENT DOCUMENTS 5,403,284 A    4/1995  Gross
5,683,365 A *  11/1997  Brown .............. A61M 25/0618
                                                604/110
(Continued)

FOREIGN PATENT DOCUMENTS

EP    0875261 A2    11/1998
JP    H09108346 A    4/1997
(Continued)

*Primary Examiner* — Kami A Bosworth
*Assistant Examiner* — Avery Smale
(74) *Attorney, Agent, or Firm* — Levenfeld Pearlstein, LLC

(57) ABSTRACT

A reuse prevention safety catheter is proposed. The reuse prevention safety catheter includes: a catheter hub having an external needle disposed therein; a cannula plug having an internal needle inserted and penetrated into the catheter hub disposed therein to introduce the external needle into a blood vessel and be separated from the catheter hub; and a locking guide unit having a through-hole configured to allow the internal needle to pass through, wherein the through-hole is deformed when the penetrated internal needle is withdrawn, such that re-penetration of the internal needle is blocked.

7 Claims, 10 Drawing Sheets

(58) Field of Classification Search
CPC .. A61M 2005/3223; A61M 2005/3224; A61M 2005/3226
See application file for complete search history.

(56) References Cited

U.S. PATENT DOCUMENTS

| | | | | |
|---|---|---|---|---|
| 5,830,190 A | * | 11/1998 | Howell | A61M 25/0631 604/168.01 |
| 2007/0185456 A1 | * | 8/2007 | Nakajima | A61M 5/3257 604/164.08 |
| 2009/0069751 A1 | * | 3/2009 | Curtis | A61M 25/0606 604/167.03 |
| 2016/0220270 A1 | | 8/2016 | Tamura et al. | |
| 2017/0049999 A1 | | 2/2017 | Kim | |

FOREIGN PATENT DOCUMENTS

| | | |
|---|---|---|
| JP | H1052499 A | 2/1998 |
| JP | 2009513267 A | 4/2009 |
| JP | 2017509455 A | 4/2017 |
| KR | 19990036967 U | 10/1999 |
| KR | 20040002700 A | 1/2004 |
| KR | 101455206 B1 | 10/2014 |
| KR | 101598469 B1 | 3/2016 |
| RU | 2276611 C2 | 5/2006 |
| RU | 2476246 C2 | 2/2013 |
| WO | 9008564 A1 | 8/1990 |
| WO | 9924092 A1 | 5/1999 |
| WO | 03026731 A1 | 4/2003 |
| WO | 2007050788 A2 | 5/2007 |
| WO | 2018163028 A1 | 9/2018 |

\* cited by examiner (a)

(b)

REUSE PREVENTION SAFETY CATHETER

CROSS REFERENCE TO RELATED APPLICATION DATA

This application is a 35 USC 371 national stage filing of PCT/KR2019/012681, filed Sep. 30, 2019, titled REUSE SAFETY PREVENTION CATHETER, which claims the benefit of and priority to Korean application 10-2019-0085075, filed Jul. 15, 2019, titled REUSE SAFETY PREVENTION CATHETER, the disclosures of which are incorporated herein in their entireties.

TECHNICAL FIELD

The present disclosure relates to a reuse prevention safety catheter which is structurally impossible to be reused after use and may be safely used.

BACKGROUND ART

A catheter is an efficient tool mainly used in a hospital for injecting a recipient with medicine. The catheter is a configuration that leaves a hub having an external needle made of a tubular material formed therein at a front end part with respect to the recipient such as a patient and the like who frequently requires medicine injection, thereby providing convenience in that it is not required to newly penetrate skin with a needle each time for medicine injection. To insert the external needle into the recipient's body, a needle of a cannula is inserted and penetrated into the external needle, such that the catheter is inserted into the recipient's body together with the external needle. After, a process of withdrawing the cannula while leaving a catheter hub is performed so that only insertion and removal of an inner needle are performed.

In modern medical science, an invasive instrument is considered as a 'taboo'. In particular, a cannular needle directly connected to infection risk should be used once unconditionally regardless of an invasive position. Since a needle is finely manufactured to be deformed when used once, there is risk of damage to tissues, such as a blood vessel and the like, when the needle is reused. Moreover, since the needle is an object inserted into and removed from a person's body, there is a great possibility to be a medium of infection.

Reuse of a disposable medical instrument such as a catheter is forbidden, but individuals who are not medical personnel heat and use a used needle sometimes by reason of insufficient hygienical common sense, expenses, and the like. Accordingly, it is required that the invasive medical instrument, such as a catheter, should be implemented to structurally prevent the reuse thereof.

As the prior art, in Korean Patent No. 10-1598469, a catheter has an irreversible operation mechanism in which a hub or a moving bar is locked or separated by a gear, a rack, and sawtooth formed on a hub and the rack blocks a path through which a needle moves to the outside after the moving bar and the hub are separated as the needle is withdrawn, such that the needle cannot be used.

However, an existing reuse prevention safety catheter requires a complex configuration for preventing reuse. With respect to features of a disposable catheter, it is clear that manufacturing cost is directly connected to profitability, but it is not preferred that a plurality of injection molded parts and a complex manufacturing process are required to implement disposability. Moreover, with respect to a structure of the existing safety catheter, a user forcibly operates the injection molded parts to set the needle at a reusable position even though it is difficult, such that it is insufficient to structurally implement a complete unusable state. Accordingly, the applicant suggests a non-reusable safety catheter capable of being implemented by using a minimum number of injection molded parts and through an extremely simple manufacturing process.

DISCLOSURE

Technical Problem

The present disclosure provides a reuse prevention safety catheter implemented at a low manufacturing cost. Moreover, the present disclosure provides a reuse prevention safety catheter which is structurally impossible to be manipulated by a user for reuse.

Technical Solution

To achieve such an objective, a reuse prevention safety catheter of the present disclosure comprises: a catheter hub having an external needle disposed therein; a cannula plug having an internal needle inserted and penetrated into the catheter hub disposed therein to introduce the external needle into a blood vessel and be separated from the catheter hub; and a locking guide unit having a through-hole configured to allow the internal needle to pass through, wherein the through-hole will be deformed when the internal needle penetrating thereinto is withdrawn, such that re-penetration of the internal needle is blocked.

Preferably, the reuse prevention safety catheter of the present disclosure further comprises a slide casing extended from the cannula plug to cover the internal needle, wherein the locking guide unit is disposed at a front end part of the slide casing.

Preferably, the slide casing further comprises a holder hooked by fingers to enable a user to separate the cannula plug from the catheter hub, wherein the locking guide unit may be disposed in the holder.

Preferably, the reuse prevention safety catheter of the present disclosure further comprises a blood blocking unit disposed in the catheter hub to block backflow of blood.

Preferably, the locking guide unit is an injection-molded part independent of the cannula plug and maintains a locked state in the cannula plug by the internal needle, wherein when a locking force is removed as the internal needle is withdrawn, an inclination is generated in the locking guide unit, such that a position of the through-hole may be changed.

Preferably, the locking guide unit comprises a first locking guide and a second locking guide, wherein since the first locking guide comes in contact with the second locking guide, a path of the through-hole configured to allow the internal needle to pass through is formed in a longitudinal direction and displacements of the first locking guide and the second locking guide may be locked by the internal needle.

Preferably, the locking guide unit has a structural shape wherein an inclination is generated therein within an angular range of greater than 0° and less than 90° by gravity, wherein the locking forces of the first locking guide and the second locking guide are removed when the internal needle is withdrawn from the locking guide unit, such that the inclination is generated in the first locking unit and the second locking unit, respectively, and a longitudinal hollow path may be collapsed by misalignment of the first locking unit and the second locking unit.

Advantageous Effects

According to the present disclosure, the reuse prevention safety catheter may be implemented with only a configuration of the locking guide which is an independent injection molded part. When one-time separation is functionally generated in the internal needle, the displacement is generated in the locking guide by the center of gravity or a structure concentrated in the angular range of greater than 0° and less than 90°, such that the position of the through-hole configured to allow the internal needle to pass through is changed. In another embodiment, since the locking guide is formed by two engaged parts, the two locking guides form one path configured to allow the internal needle to pass through while being engaged with each other, and each of the parts is misaligned when the internal needle is withdrawn, such that the path for the internal needle is collapsed, thereby preventing reinsertion. In other words, since the position of the through-hole configured to allow the internal needle to pass through or the structure of the through-hole is changed, the locking structure of the present disclosure implements the path of the internal needle in a one-time manner.

At this time, since the internal needle is received in the through-hole inside the cannula plug, a user cannot intentionally adjust the angle of the internal needle. Accordingly, even though the user intentionally shakes the tilted locking guide to adjust the angle thereof, aligning a penetration angle of the internal needle and the through-hole of the locking guide on the same axis requires work of inserting the internal needle into the through-hole in a state in which the locking guide with the functionally concentrated center of gravity is locked at a normal position without a separate structure, thereby being almost impossible. Accordingly, the reuse prevention safety catheter according to the present disclosure provides advantage of being difficult to dismantle an irreversible mechanism in spite of the user's efforts.

Moreover, a manufacturing process of the reuse prevention safety catheter according to the present disclosure also performs an ordinary assembly process of inserting and penetrating the internal needle into the locking guide, such that the reuse prevention safety catheter may be manufactured through simple work. Accordingly, the present disclosure provides advantage of being implemented at low manufacturing costs to be especially suitable for the feature, such as disposability, of the catheter.

BEST MODE

Figure 1:
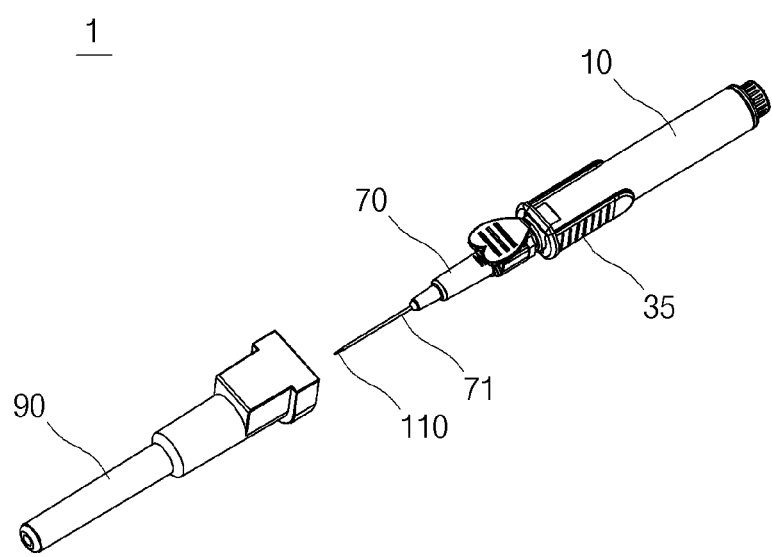
FIG. 1 is a perspective view showing a reuse prevention safety catheter according to an embodiment of the present disclosure.

Hereinafter, with reference to the contents described in the accompanying drawings, the present disclosure will be described in detail. However, the present disclosure is not limited or limited by the exemplary embodiments. Like reference numerals in the drawings denote members that perform substantially the same function.

The objectives and effects of the present disclosure may be naturally understood or made more apparent from the following description, and the objectives and effects of the present disclosure are not limited only by the following description. In addition, in describing the present disclosure, when it is determined that the detailed description of known technology related to the present disclosure may unnecessarily obscure the subject matter of the present disclosure, the detailed description thereof will be omitted.

FIG. 1 is a perspective view showing a reuse prevention safety catheter according to an embodiment of the present disclosure. The reuse prevention safety catheter 1 according to the embodiment of the present disclosure comprises a cannula plug 10, a slide casing 30 (FIG. 3), a locking guide 40 (FIG. 4), a catheter hub 70, and a cap 90.

The cap 90 is coupled to the catheter hub 70 before the internal needle 110 is inserted into a recipient's body to prevent an end of the internal needle 110 from being exposed to the outside. When the internal needle 110 is inserted into the recipient's body to use the reuse prevention safety catheter 1 according to the present disclosure, the cap 90 is configured to be separated and removed therefrom. With reference to FIG. 1, the reuse prevention safety catheter 1 is shown in a state in which the cap 90 is separated from the reuse prevention safety catheter 1 before use. In the reuse prevention safety catheter 1, the slide casing 30 received in the cannula plug 10 is extended as the internal needle 110 is withdrawn from the recipient's body after injection. Simultaneously with extending the slide casing 30, the catheter hub 70 is separated from the cannula plug 10 and the slide cover 30 covers the peripheral of the internal needle 110 escaping from the catheter hub 70. When the slide casing 30 is completely extended after completion of one-time use of the reuse prevention safety catheter 1, an irreversible mechanism should be implemented to prevent the slide casing 30 from entering the cannula plug 10 again. In particular, the slide casing 30 according to the present embodiment does not have a separate coupling configuration for locking, but a locking guide 50 blocks an end of the internal needle 110 in spite of the absence of the coupling configuration, such that it is prevented that the slide casing 30 is inserted in the direction of the cannula plug 10. In this regard, it will be described later in FIG. 4.

Figure 2:
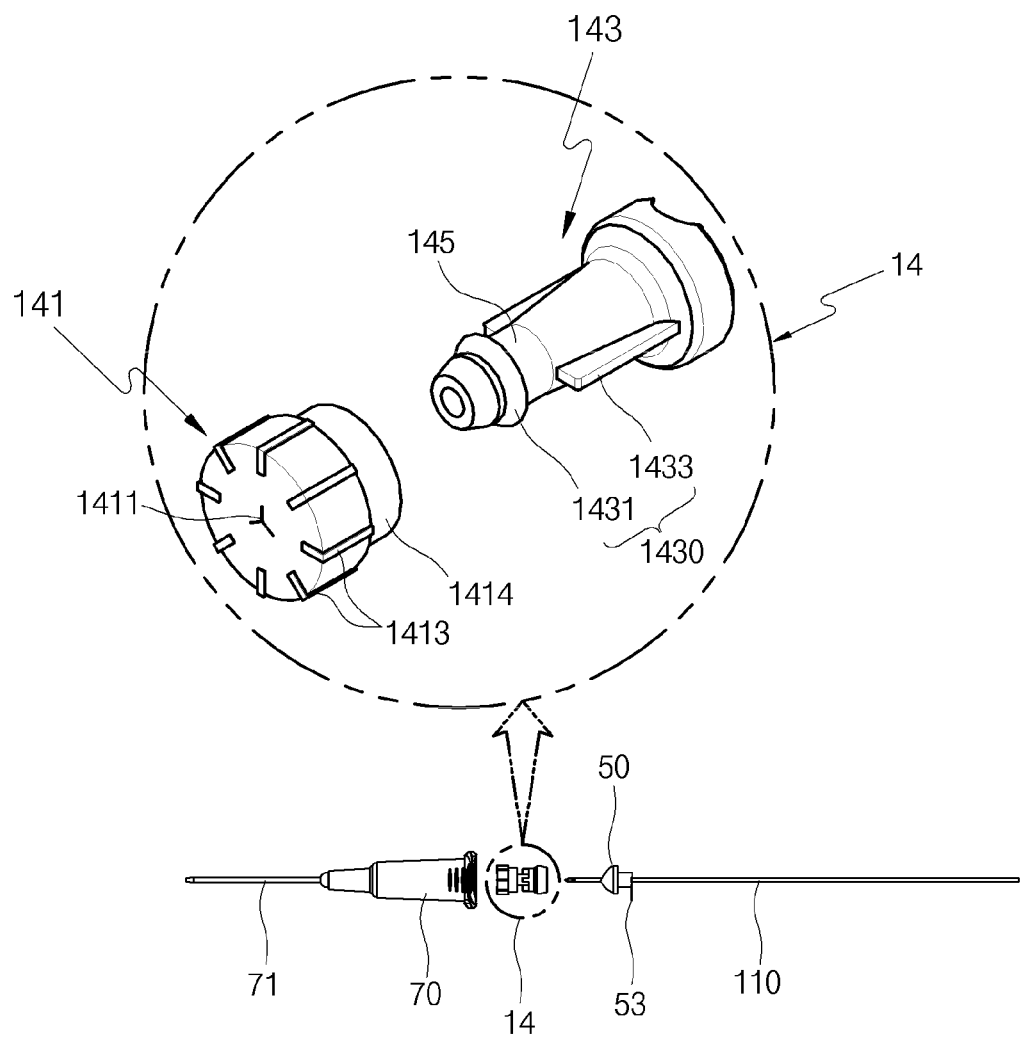
FIG. 2 shows a catheter hub and a blood blocking unit according to the embodiment of FIG. 1.

FIG. 2 shows the catheter hub 70 and the blood blocking unit 14 according to the embodiment of the present disclosure. FIG. 2 separately shows the catheter hub 70 having an external needle 71 disposed therein and the blood blocking unit 14 disposed in the catheter hub 70 to block backflow of blood. The blood blocking unit 14 is inserted into a through-hole inside the catheter hub 70. On the other hand, FIG. 2 simultaneously shows the internal needle 110 extended from the catheter hub 70 and the locking guide 50 to allow the internal needle 110 to be inserted thereinto and pass through. To show a coupling relation between the internal needle 110 and the locking guide 50, the slide casing 30 covering the outer circumference of the internal needle 110 is omitted in FIG. 2.

The blood blocking unit 14 may comprise a blood blocking holder 143 and a blood blocking gasket 141. One-time medicinal fluid supply into a blood vessel is completed by one-time puncture of a syringe. On the other hand, in the case of requiring continuous medicinal fluid supply, such as a transfusion and a Ringer solution, the catheter hub 70 should be used to intermediate a connection tip of medicinal fluid to the blood vessel. During this process, a process of introducing an internal needle cannula for initial blood vessel invasion and a process of removing the internal needle cannula to be coupled to the connection tip after completion of the invasion are performed in the catheter hub 70. At this time, when the internal needle cannula is removed, the blood may flow back to the catheter hub 70 inserted into the blood vessel. Accordingly, it is preferred to block the backflow of blood in a process of removing the cannula. For the sake of clear explanation of the present embodiment, it is called first blocking that the backflow of blood is blocked in the process of removing the internal needle cannula.

On the other hand, after the connection tip is connected to the catheter hub 70 without the backflow of blood due to first blocking and the medicinal fluid is sufficiently supplied to a patient, a situation, in which the connection tip should be temporarily separated or replaced from the connection tip as necessary, frequently occurs. When the connection tip is separated, the backflow of blood flowing back to the catheter hub 70 should be blocked like as first blocking. For the sake of clear explanation of the present embodiment, it is called second blocking that the backflow of blood is blocked during the process of removing the connection tip.

The blood blocking gasket 141 is received in the internal space of the catheter hub 70 and may be an elastic material which has a cut hole 1411 that is restored in separation of the internal needle 110 to close the front end of the catheter hub 70 while allowing entrance and exit of the internal needle 110 of the cannula. According to the present embodiment, the blood blocking gasket 141 may be provided with a silicone rubber composite material having rigidity capable of securing predetermined elasticity and restoration force.

The blood block gasket 141 may comprise an upper disk 1413 and a lower disk 1414. The upper disk 1413 and the lower disk 1414 may be integrally formed. The upper disk 1414 is inserted into and fixed in the front end direction of a body of the catheter hub 70 to close the front end of the catheter hub 70, thereby having a function of a valve for blocking the backflow of blood.

The upper disk 1414 has the cut hole 1411 formed therein and may perform a function of a valve for blocking the backflow of blood by opening and closing the cut hole 1411. According to the present embodiment, the cut hole 1411 may be formed by cut passing through the upper disk 1413. It is no matter that the number of cuts formed in the cut hole 1411 is one formed by cutting once the cut hole 1411, but as shown in the present embodiment, three cuts having a central connection point at 120° are formed to smoothly open and close the cut hole 1411.

The upper disk 1413 may be formed by a predetermined thickness to have a restoration force that allows the cut hole 1411 to push the front end part 1430 of the blood blocking holder 143 in separation of the internal needle 110 of the cannula or the connection tip to close the cut hole 1411. According to the present embodiment, it is preferred that the upper disk 1413 has a thickness of 0.5-1.2 mm.

The lower disk 1414 refers to a rear end configuration of the blood blocking gasket 141 into which the front end part 1430 of the blood blocking holder 143 is inserted. The lower disk 1414 receives the front end part 1430 of the blood blocking holder 143 through a lower coupling hole. Since a second step 1431 of the blood block holder 143 is closely attached and locked to the internal surface of the coupling hole, the lower disk 1414 is disposed to allow the front end part 1430 of the blood blocking holder 143 to be received in the internal space of the blood blocking holder 143 without a gap while being closely attached to the lower surface of the upper disk 1413.

It is preferred that the height of the internal space of the lower disk 1414 is configured to correspond to a distance from a front end of the front end part 1430 of the blood blocking holder 143 to the lower surface of the second step 1431. Accordingly, when there is no separate external force, the front end of the blood blocking holder 143 is disposed inside the lower disk 1414 while being closely attached to the lower surface of the upper disk 1413 without a gap.

The blood blocking holder 143 is coupled to the connection tip for injecting the medicinal fluid after separation of the internal needle 110 to be pressed and the front end part 1430 received inside the blood blocking gasket 141 presses the cut hole 1411 in the front end direction without penetrating the cut hole 1411 to operate the cut hole 1411.

The blood blocking holder 143 has a penetrated medicinal fluid injection path formed therein and the front end thereof has a wedge shape structure. A distal part is formed at the rear end of the blood blocking holder 143 in a taper shape with an internal diameter that is gradually increased and the connection tip is closely pressed to the rear end of the blood blocking holder 143, such that the connection tip may be coupled to the catheter hub 70.

The blood blocking holder 143 has a stopper formed therein to limit a region moving in the front end direction of a body 11 to be operated within a range through which the blood blocking gasket 141 does not pass. The blood blocking holder 143 has a first step 1433 protruding from a proximal part to function as a stopper and has the second step 1431 formed at the front end part to be received inside the blood blocking gasket 141, and the width of a groove 145 that is formed by the first step 1433 and the second step 1431 may define an operation range of the front end part 1430.

The width of the groove 145 may be greater than the thickness of a lower disk 1414 coupler. Since the length of the groove 145 may be greater than the thickness of the lower disk 1414 coupler, a predetermined spacing distance exists in the front end part 1430 received in the lower disk 1414.

In the blood blocking holder 143, the first step 1433 may function as the stopper and a region from the first step 1433 to the front end may be defined by the front end part 1430 received inside the blood blocking gasket 141. According to the present embodiment, the first step 1433 may be formed on both side surfaces of the blood blocking holder 143 in a wing shape. In the present embodiment, the first step 1433 that protrudes from the blood blocking holder 143 to perform a function of preventing penetration of the blood blocking gasket 141 is shown in the wing shape easy to manufacture, but other protruding structures are possible.

In the blood blocking holder 143, when the connection tip is coupled to the catheter hub 10, the front end of the connection tip presses the rear end of the blood blocking holder 143, such that an operation of moving forward a predetermined distance is performed. Moreover, in the blood blocking holder 143, when the connection tip is separated from the catheter hub 70, an external force pressing the rear end of the blood blocking holder 143 is released, such that an operation of moving backward by the restoration force of the upper disk 1413 is performed. In the present description, such a distance that the blood blocking holder 143 moves forward or backward as the blood blocking holder 143 is connected to or disconnected from the connection tip refers to an operation range. The blood blocking holder 143 has the operation range in which the front end part 1430 moves forward in the direction of the upper disk 1413 by a distance from a stop state of being received in the lower disk 1414 to a degree capable of opening the cut hole 1411.

The blood blocking unit 14 of FIG. 2 comprises two independent injection molded products in which a blood block gasket 141 and a blood blocking holder 143 are coupled to each other, and may perform a function of blocking the backflow of blood with only the two injection molded parts. The blood blocking unit 14 is manufactured by a separate process to be assembled in the catheter hub 70.

Figure 3:
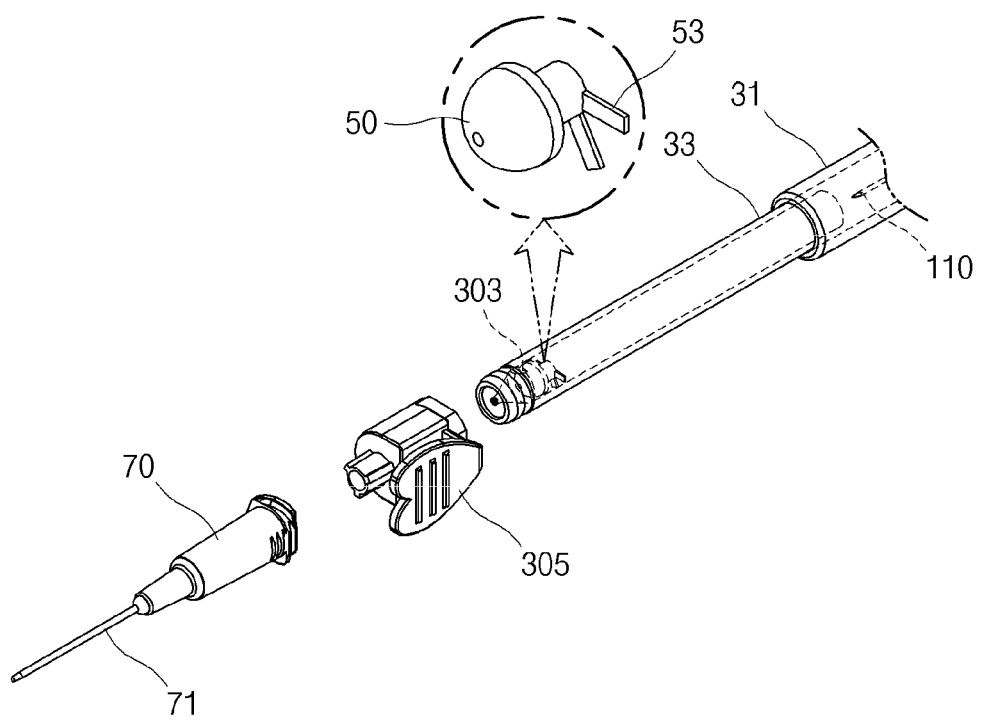
FIG. 3 is an exploded perspective view showing a front end part of the reuse prevention safety catheter according to the embodiment of FIG. 1.

FIG. 3 is the exploded perspective view showing the front end part of the reuse prevention safety catheter according to the embodiment of the present disclosure. With reference to FIG. 3, the front end part from which the catheter hub 70 is separated comprises: a holder 305; the slide casing 30; and the locking guide 50 received on the slide casing 30.

The slide casing 30 has the through-hole formed therein and is withdrawn from the cannula plug 10 to cover the internal needle 110. More precisely, the slide casing 30 is withdrawn in an operation of separating the cannula plug 10 from the catheter hub 70. Due to the operation, the slide casing 30 not only covers the internal needle 110, but also is withdrawn more than the internal needle 110 until the locking guide 50 is separated from the internal needle 110.

According to the present embodiment, the slide casing 30 may be provided in a multistage type. In the present embodiment, the slide casing 30 formed in two stages is provided. The slide casing 30 comprises: a first slide 31 withdrawn from the inside of the cannula plug 10; and a second slide 33 withdrawn from the inside of the first slide 31. Since the first and second slides 31, 33 may be designed to correspond to the length of the cannula plug 10, the slide casing 30 may be withdrawn by twice of the length of the cannula plug 10. The withdrawn length of the slide casing 30 exceeds the length of the internal needle 110 and the length (height direction) of the locking guide 50.

Accordingly, in the case of designing the cannula plug 10 slightly short to implement the catheter in a small size, the reuse prevention safety catheter 1 according to the present embodiment may use the slide casing 30 of a multistage configuration (for example, two stages) to cover the internal needle 110 slightly lengthily exposed from the cannula plug 10. On the other hand, according to another embodiment, when the cannula plug 10 of the reuse prevention safety catheter is designed in a sufficient length, the exposed internal needle 110 may be covered even though only a one-stage slide casing is used. The slide casing 30 described in the present embodiment is formed in a two-stage type, but may be formed in a one-stage type when the length may exceed the length of the internal needle 110 capable of escaping the locking guide 50.

The slide casing 30 further comprises a holder 305 hooked by fingers to enable a user to separate the cannula plug 10 from the catheter hub 70. It is satisfied that the shape of the holder 305 has a structure capable of being projected or forming friction to enable an operator to push up the slide casing with the fingers. The holder 305 is disposed to be coupled to the front end of the slide casing 30.

After the reuse prevention safety catheter 1 according to the present embodiment is invaded in a recipient's skin, the operator pushes up the holder 305 by an index finger while holding the cannula plug 10 by fingers except for the index finger. In this case, since the internal needle 110 is in a state of being coupled to the cannula plug 10 and a plug bar 11 (FIG. 6), the internal needle 110 moves backward with the cannula plug 10. The internal needle 10 moves backward with the cannula plug 10 and, at the same time, the slide casing 30 moves with respect to the cannula plug 10. To explain configurations of the reuse prevention safety catheter 1, it is represented that the slide casing 30 is extended from the cannula plug 10. However, in consideration of a real operation, to be exact, the cannula plug 10 moves backward from the slide casing 30 and the folded slide casing 30 is exposed to the outside due to retraction of the cannula plug 10, such that the slide casing 30 covers the outside of the internal needle 110.

At this time, it is emphasized that the reuse prevention safety catheter 1 according to the present embodiment does not require a separate locking means for preventing the slide casing 30 from moving backward into the cannula plug 10 again. The slide casing 30 may be manufactured only to slide with respect to the cannula plug 10 and cannot perform an operation of naturally moving backward from a mechanism, to be described later, for blocking the internal needle 110 of the locking guide 50 in the direction of the cannula plug 10. Accordingly, it is not required to form a complex coupling structure on the slide casing 30 and the reuse prevention safety catheter 1 may be implemented at low manufacturing costs.

The slide casing 30 has a protrusion part 303 formed on the internal wall surface of an upper part to prevent separation of the locking guide. The protrusion part 303 formed in the slide casing 30 is a configuration, which interacts with the locking guide, to be described later and will be described later in detail in FIG. 4. The protrusion part 303 is difficult to be visually checked in an internal exploded view of the slide casing of FIG. 3, such that it is preferred to be referred through a cross-sectional view of FIG. 4.

The slide casing 30 uses the configuration of the protrusion part 303 formed therein to prevent the locking guide 50 from being separated from the internal front end part of the slide casing 30. The protrusion part 303 locks the locking guide 50 when the internal needle 110 is separated from the catheter hub 70, such that the internal needle 110 may be separated from the locking guide 50. When assembling the reuse prevention safety catheter 1, a manufacturer inserts and penetrates the locking guide 50 into the internal needle 110 and fits the internal needle 110 to the slide casing 30. At this time, as the locking guide 50 is inserted into the slide casing 30, the protrusion part 303 is slightly locked and enables the manufacturer to sense that the locking guide 50 passes through the protrusion part 303. Through such a process, the reuse prevention safety catheter 1 according to the present embodiment is completely assembled. Even though a reuse prevention function exists, the reuse prevention safety catheter 1 according to the present embodiment does not require additional manufacturing labor in comparison with assembly of an ordinary catheter.

The locking guide 50 is disposed inside the slide casing 30 and has a structure that has an eccentric center of gravity while having the through-hole configured to allow the internal needle 110 to pass through, such that an end of the internal needle 110 is blocked by displacement generated when the internal needle 110 is withdrawn. The locking guide 50 satisfies a structure that generates an inclination within an angular range of 0° to 90°.

Due to features of operation, the catheter allows the internal needle 110 to be invaded within an angular range of greater than 0° to less than 90°. After invasion, the internal needle 110 is withdrawn within an angular range of greater than 0° to less than 90°. When a separate fixing member does not exist within an angular range of greater than 0° to less than 90° with respect to the ground, the inclination due to the eccentric center of gravity is generated in the locking guide 50 and such a displacement of the locking guide 50 changes the position of the through-hole configured to allow the internal needle 110 to pass through.

Briefly, as the internal needle 110 penetrating the locking guide 50 is withdrawn, the locking guide 50 is inclined in the slide casing 30 due to the eccentric center of gravity and the position of the through-hole configured to allow the internal needle 110 to pass through is changed by generation of the displacement at this time, such that the locking guide 50 is blocked from being penetrated again by the internal needle 110. Due to the protrusion part 303, the position of the locking guide 50 is maintained at the front end part of the slide guide 30. When a user wants to reuse the internal needle 110, the user has to move backward the slide casing 30 into the cannula plug 10. When the position of the through-hole configured to allow the internal needle 110 to pass through is changed by the generation of displacement, even though the user wants to move back the slide casing 30 into the cannula plug 10, the locking guide 50 according to the present embodiment prevents the internal needle 110 from passing therethrough, such that the slide casing 30 is prevented from being returned to an appearance before use.

The locking guide 50 may comprise one or more rib 53 structures inducing inclination by gravity. In the present description, the terminology of a rib 53 may collectively refer to portions causing the eccentric center of gravity in the locking guide. In other embodiments, the rib 53 may be a member that causes asymmetry in the structure of the locking guide 50. With reference to FIG. 3, the ribs 53, which are a structure that causes the asymmetry in the structure of the locking guide 50, show a case of pushing the internal wall surface of the slide casing 30 to cause the inclination of the locking guide 50.

Figure 4:
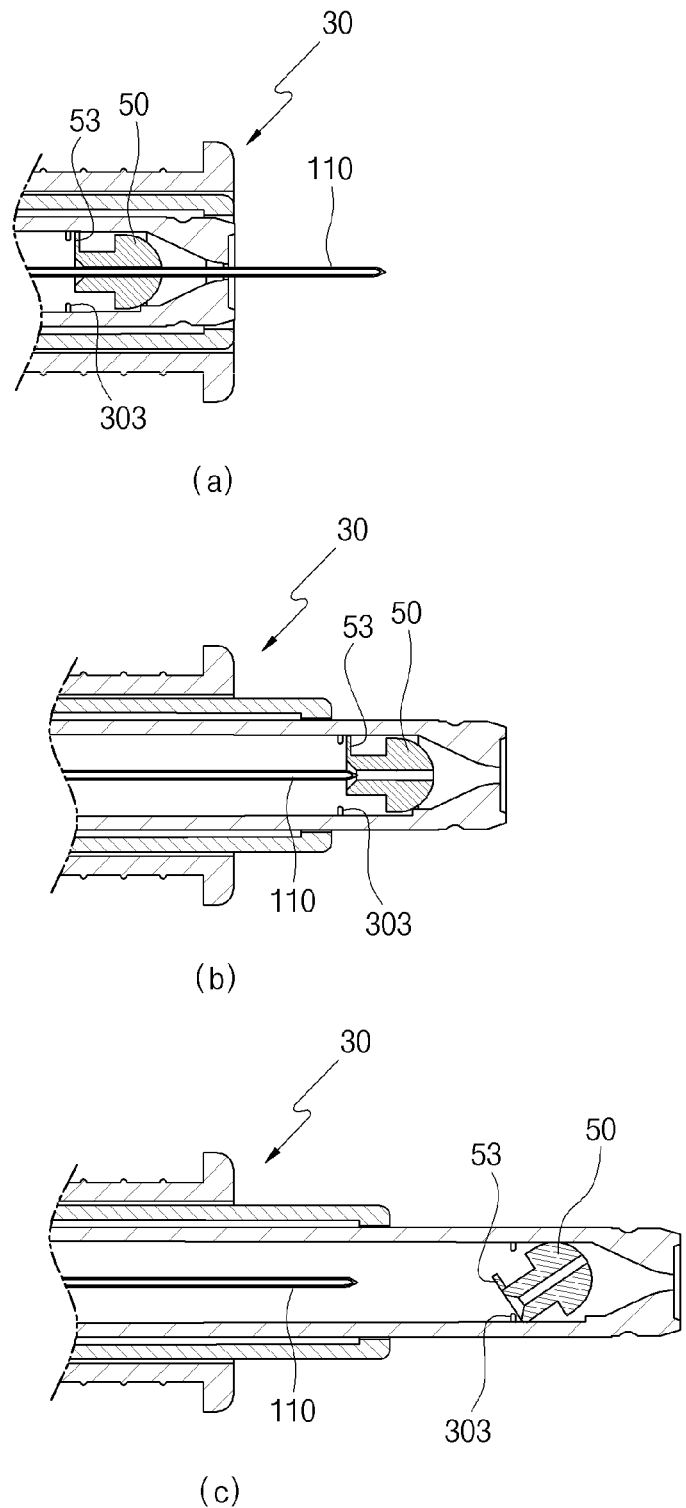
FIG. 4 shows an operation mechanism of a locking guide according to the embodiment of FIG. 1.

FIG. 4 shows the operation mechanism of the locking guide 50 according to the present embodiment. (a) of FIG. 4, which is the appearance before use of the reuse prevention safety catheter 1, shows a state in which the slide casing 30 is folded in the cannula plug 10. To easily understand the mechanism, the catheter hub 70 coupled to the front side of the internal needle 110 is omitted in FIG. 4. (b) of FIG. 4 shows a state in which the internal needle 110 is withdrawn after use of the reuse prevention safety catheter 1. As the internal needle 110 moves backward with the cannula plug 10, the slide casing 30 is relatively withdrawn. At this time, (b) of FIG. 4 shows a state in which the internal needle 110 is inserted into the through-hole of the locking guide 50 that is insufficiently moved backward yet, and an insertion state of the internal needle 110 provides a locking force to prevent displacement from being generated in the locking guide 50.

(c) of FIG. 4 shows a state in which the internal needle 110 is escaped from the locking guide 50 to be sufficiently withdrawn. With reference to (c) of FIG. 4, when the internal needle 110 is separated from the locking guide 50, the locking force for maintaining the posture of the locking guide 50 is removed. As the center of gravity is concentrated, the inclination is generated in the locking guide 50. With reference to the locking guide 50 of FIG. 4, since the rib 53 pushes the internal wall surface of the slide casing 30, the posture of the locking guide 50 is more collapsed. Due to the generated displacement, in the locking guide 50, the position of the through-hole through which the internal needle 110 may pass again is changed to make reinsertion impossible. It is considerable that, when there is no separate locking force, the inclination is structurally generated in the locking guide 50. Accordingly, the user cannot place the locking guide at a correct position in the slide casing 30 having the closed inside. Moreover, since the internal needle 110 is also locked in the cannula plug 10, the internal needle 110 cannot be operated to place the locking guide 50 at the correct position.

Figure 5:
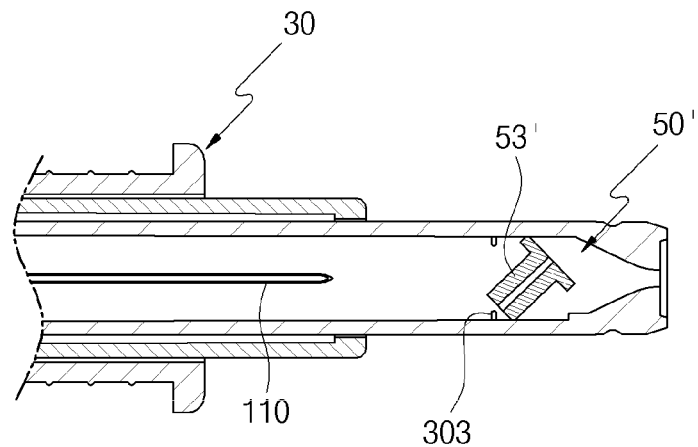
FIG. 5 shows a locking guide according to another embodiment of FIG. 1.
Figure 5:
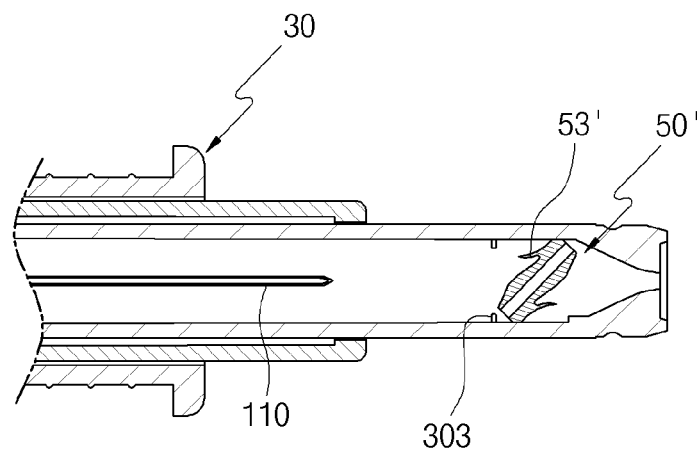

FIG. 5 shows the locking guide 50' according to another embodiment of the present disclosure. With reference to (a) of FIG. 5, the locking guide 50' has a shape with the eccentric center of gravity within the angular range of greater than 0° and less than 90° with respect to the ground and may have a T-shaped structure. The T-shaped locking guide 50' may be naturally inclined at any angle except for a vertical angle.

As another embodiment, with reference to (b) of FIG. 5, the locking guide 50' is provided in a point-symmetric shape, wherein a rib 53' guiding the inclination at two points of upper and lower parts may be formed in the locking guide 50'. In this case, the rib 53' may be provided with a safer and more advantageous structure than an embodiment of an existing locking guide that guides the inclination at one point.

Figure 6:
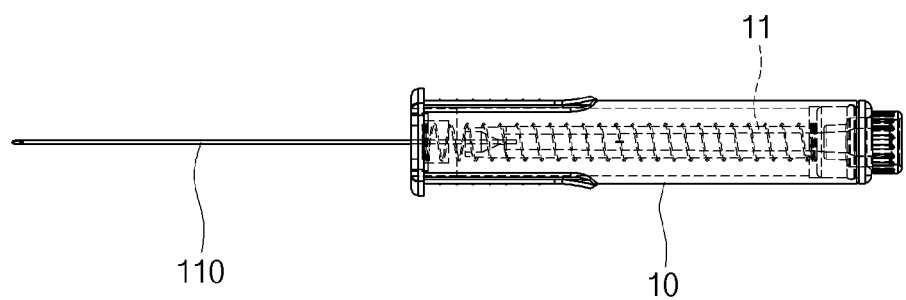
FIG. 6 shows a cannula plug and an internal needle according to the embodiment of FIG. 1.

FIG. 6 shows the cannula plug 10 and the internal needle 110 according to the embodiment of the present disclosure. The internal needle 110 inserted and penetrated into the catheter hub is provided in the cannula plug 10. The cannula plug 10 introduces the catheter hub 70 to allow invasion of the external needle 71 and then is removed together with the internal needle 110. As described in background art, the cannula plug 10 and the internal needle 110 should be discarded after one-time invasion.

The cannula plug 10 has a hollow internal space. A needle, which is the internal needle 110, is disposed at the innermost position in the internal space of the cannula plug 10. The internal needle 110 is coupled to the plug bar 11, which has a predetermined length in consideration of the design of a length capable of being inserted and penetrated into the catheter hub 70, to be received in the cannula plug 10.

The slide casing 30 may be provided on the outside of the internal needle 110 in the internal space of the cannula plug. The slide casing 30 may be received inside the cannula plug 10 to be extended from the cannula plug 10. The cannula plug 10 has a configuration held by the operator with fingers except for the index finger to extend the cannula plug 10 from the catheter hub 70 after the user is punctured by the internal needle 110. At this time, to facilitate the extension operation of the operator, the cannula plug 10 may have a corrugated surface on the outer circumference thereof to generate friction.

Figure 7:
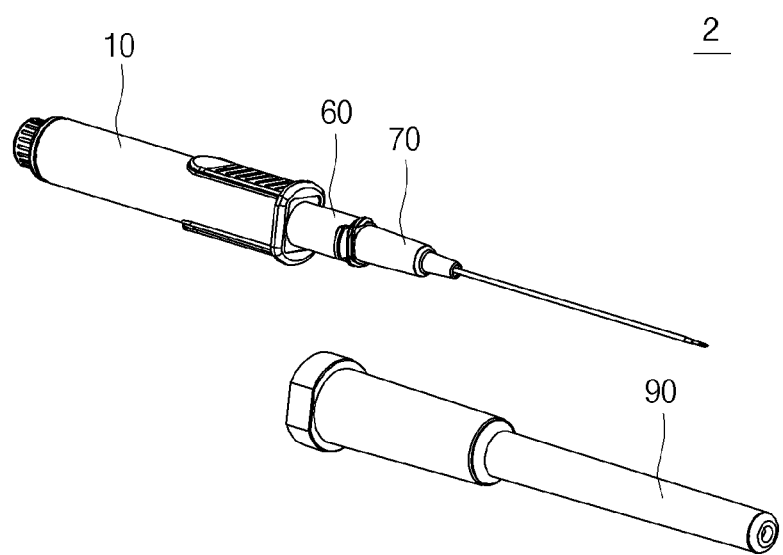
FIG. 7 is a perspective view showing a reuse prevention safety catheter according to another embodiment of the present disclosure.

FIG. 7 is a perspective view of a reuse prevention safety catheter 2 according to another embodiment of the present disclosure. With reference to FIG. 7, the reuse prevention safety catheter 2 according to the present embodiment may comprise a catheter hub 70, a cannula plug 10, and a locking guide unit 5. The present embodiment discloses another embodiment of the locking guide 50 described in FIGS. 1 to 6. The locking guide unit 5 may apply the configuration of the locking guide 50 described above, but an embodiment of an improved locking guide 50 is disclosed in FIGS. 7 to 9 to be described hereinafter.

FIG. 7 shows the reuse prevention safety catheter 2 applying the embodiment of an added holder 60 and the embodiment of a modified locking guide unit 5 thereto, and other configurations are the same as that described in FIGS. 1 to 6.

Figure 8:
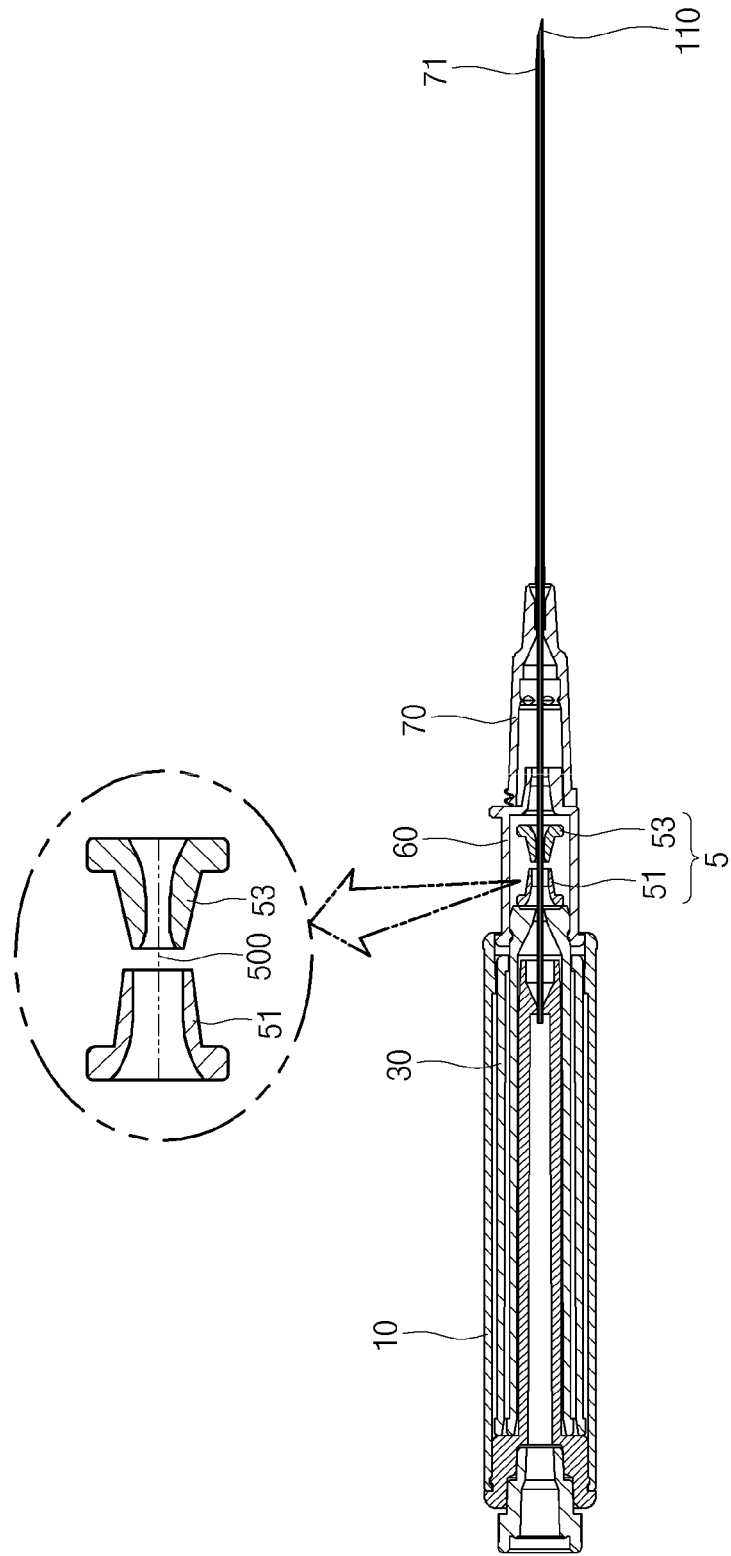
FIG. 8 shows a catheter hub and a blood blocking unit according to the embodiment of FIG. 7.

FIG. 8 shows the holder 60 and the locking guide unit 5 according to the embodiment of FIG. 7.

The locking guide unit 5 according to the present embodiment has a through-hole 500 formed therein to allow the internal needle 110 to pass through, wherein the through-hole 500 is deformed in withdrawal of the penetrating internal needle 110, such that repenetration of the internal needle 110 is blocked. Deformation of the through-hole 500 formed by the locking guide unit 5 comprehensively means the embodiment prescribed above in which the position of the through-hole 500 is changed like as FIGS. 1 to 6 and an embodiment to be described hereinafter in which the path of the through-hole 500 is collapsed and deformed. In the embodiment prescribed above in which the position of the through-hole 500 is changed like as FIGS. 1 to 6, the locking guide unit 5 is an injection molded part independent of the cannula plug 10 and maintains a state in which the internal needle 110 is locked in the cannula plug 10, wherein, when the locking force is removed since the internal needle 110 is withdrawn, the inclination is generated, such that the position of the through-hole 500 is changed.

With reference to FIG. 8, the locking guide unit 5 according to the present embodiment may be provided in the holder 60. On the other hand, as described in FIGS. 1 to 6, the locking guide unit 5 may be received in the front end of the slide casing 30. Hereinafter, the embodiment of the locking guide unit 5 in which the path of the through-hole 500 is collapsed is described.

The locking guide unit 5 includes a first locking guide 51 and a second locking guide 53, the through-hole 500 through which the internal needle 110 may pass is formed in a longitudinal direction since the first locking guide 51 comes in contact with the second locking guide 53, and displacements of the first locking guide 51 and the second locking guide 53 are fixed by the internal needle 110.

The locking guide unit 5 is provided in a structural shape that generates inclination by gravity within an angular range of greater than 0° and less than 90°, and the locking force of the first locking guide 51 and the second locking guide 53 is removed as the internal needle 110 is withdrawn, such that the inclination is generated in the first locking guide 51 and the second locking guide 53 and the path of the longitudinal through-hole 500 may be collapsed by misalignment between the first locking guide 51 and the second locking guide 53.

Figure 9:
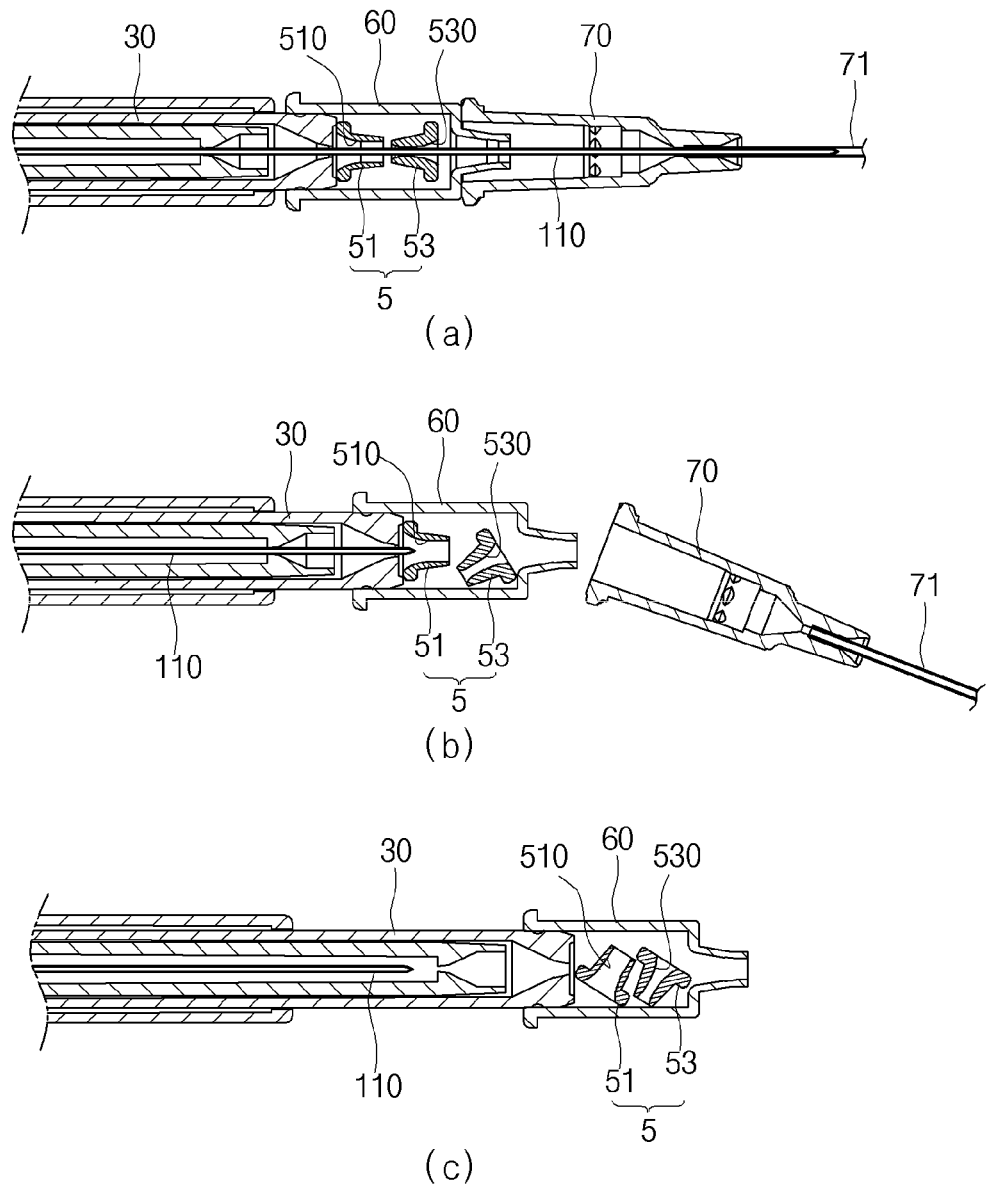
FIG. 9 shows an operation mechanism of a locking guide according to the embodiment of FIG. 7.

FIG. 9 shows the operation mechanism of the locking guide unit 5 according to the embodiment of FIG. 7. With reference to (a) of FIG. 9, the first locking guide 51 has a first through-hole 510 formed therein to allow the internal needle 110 to pass through. The second locking guide 52 also has a second through-hole 530 formed therein to allow the internal needle 110 to pass through. As the internal needle 100 penetrates the first locking guide 51 and the second locking guide 53, the first locking guide 51 and the second locking guide 53 are aligned on an axis and are locked in the holder 60 by the internal needle 110.

With reference to (b) of FIG. 9, it may be checked that the internal needle 100 is in a state in which the internal needle 110 moves backward from the second through-hole 530 by a distance capable of withdrawing the internal needle 110. As a user pushes up the holder 60, the slide casing 30 is extended to cover the internal needle 110, and the internal needle 110 moves backward and is separated from the guide unit 5.

With reference to (c) of FIG. 9, it may be checked that the holder 60 is sufficiently pushed up, so the slide casing 30 is maximally withdrawn and the cannula plug 10 is completely separated from the catheter hub 70. A view of (c) of FIG. 9, in which the cannula plug 10 is completely separated from the catheter hub 70 after invasion of the internal needle 110, shows the reuse prevention safety catheter 2 after one-time use. In this case, the internal needle 110 is completely separated from the locking guide unit 5, such that the locking forces of the first locking guide 51 and the second locking guide 53 are released. When the locking forces of the first locking guide 51 and the second locking guide 53 are released, each of the first locking guide 51 and the second locking guide 53 is freely inclined in the holder 60, such that two parts are randomly separated and received. Accordingly, axial alignment of the first through-hole 510 and the second through-hole 530 is naturally collapsed. As a result, the path of the single through-hole 500, which is a penetration path of the internal needle 110, is collapsed. After this, even though a user wants to move forward the internal needle 110 for reuse, the internal needle 110 is locked on the locking guide unit 5 since the path of the through-hole 500 is collapsed. Accordingly, the slide casing 30 extended once cannot move backward to a needle block of the locking guide unit 5, so the irreversible mechanism is formed. As shown in the present embodiment, in the case in which the locking guide unit 5 is implemented by two parts, no matter how hard the user try, the internal needle 110 cannot be set at a position for reuse.

Figure 10:
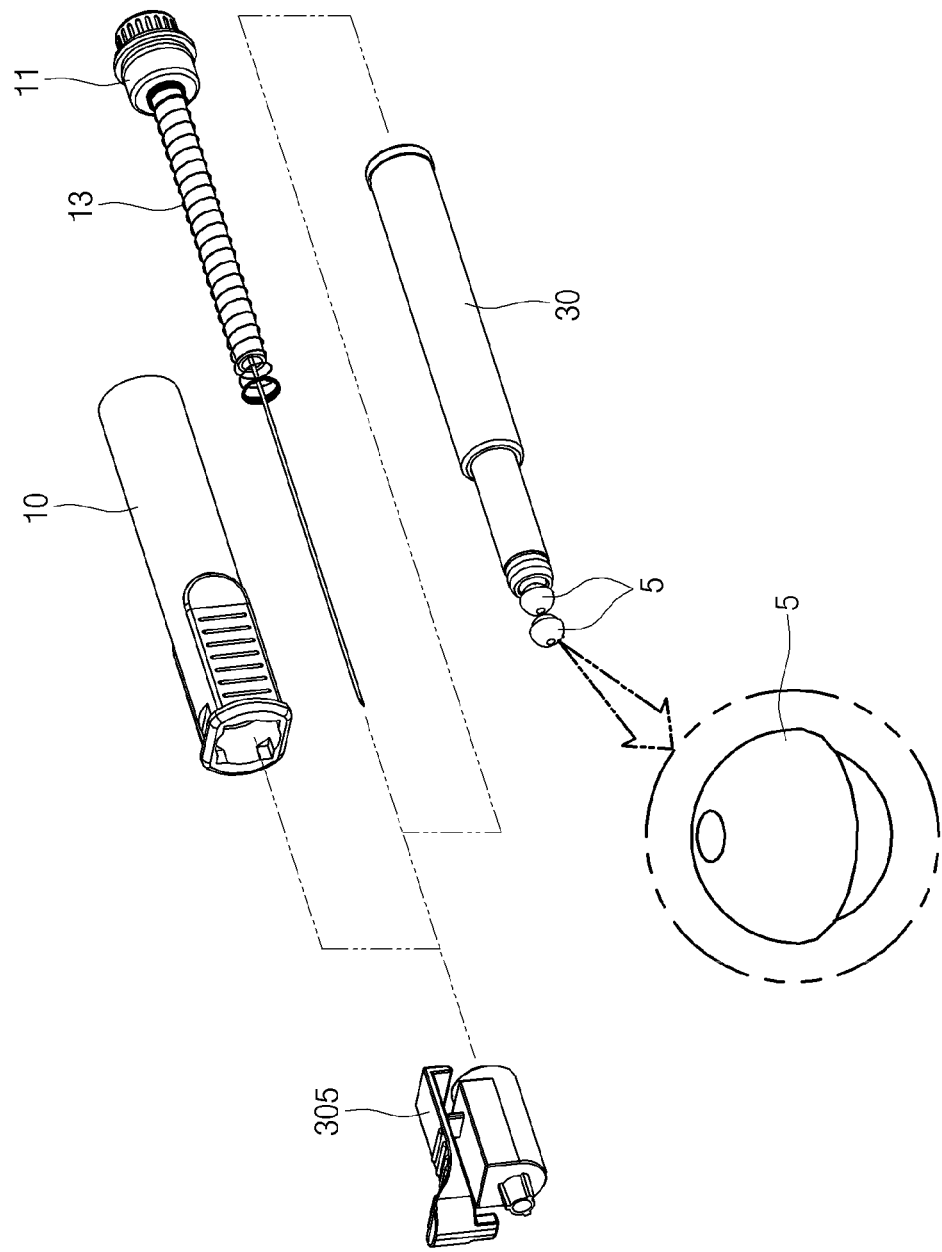
FIG. 10 is an exploded perspective view showing a reuse prevention safety catheter according to another embodiment of the present disclosure.

FIG. 10 is an exploded perspective view showing a reuse prevention safety catheter 1 according to another embodiment of the present disclosure. In the embodiment of the reuse prevention safety catheter 1 in FIG. 10, the structures of the holder 305 and the locking guide unit 5 are modified and a configuration of a spring 13 is added thereto.

After the catheter hub 70 is invaded in a blood vessel, the holder 305 is supported by the user's fingers to facilitate separation of the cannula plug 10 from the catheter hub 70. In this process, the user supports the holder 305 and has to push up the slide casing 30 to the end until the internal needle 110 is completely separated from the locking guide unit 5. If the user pushes up the slide casing 30 without completely separating the internal needle 110 from the locking guide unit 5, the above-mentioned path block of the internal needle 110 for preventing reuse is not formed. Accordingly, in the embodiment of FIG. 10, the spring 13 is disposed in the plug bar 11. The spring 13 goes into the slide casing 30 and pushes up the slide casing 30 up to the end by elastic force. Accordingly, it may be guaranteed that the internal needle 110 is separated from the locking guide unit 5 without the user's manual operation. Initial fixation of the spring 13 may be implemented by a coupling part 307 (FIG. 11) of the hub 305.

With respect to the locking guide unit 5, only the structural shape of the outer circumference of the locking guide 50 described in FIGS. 1 to 9 is changed. In the embodiments of FIGS. 7 to 10, the locking guide unit 5 comprises the two locking guides 50. When the internal needle is separated from the locking guide unit 5 that comprises the two locking guides 50, the state of the two locking guides 50 should be changed to make the two locking guides 50 misaligned each other. The embodiment of FIG. 10 provides a two-stage domical locking guide having different inner diameters to facilitate deformation of the through-hole of the locking guide unit 5. The locking guide disclosed in FIG. 10 has a shape in which an upper part has a large inner diameter and the inner diameter of a lower part is less than that of the upper part. Since both of the upper and lower surfaces of the locking guide have a domical round structure, the structure easily generates the inclination. In another embodiment, the locking guide unit 5 may have a groove formed on a facing contact surface to easily generate misalignment when the internal needle 110 is withdrawn and the locking force is removed.

Figure 11:
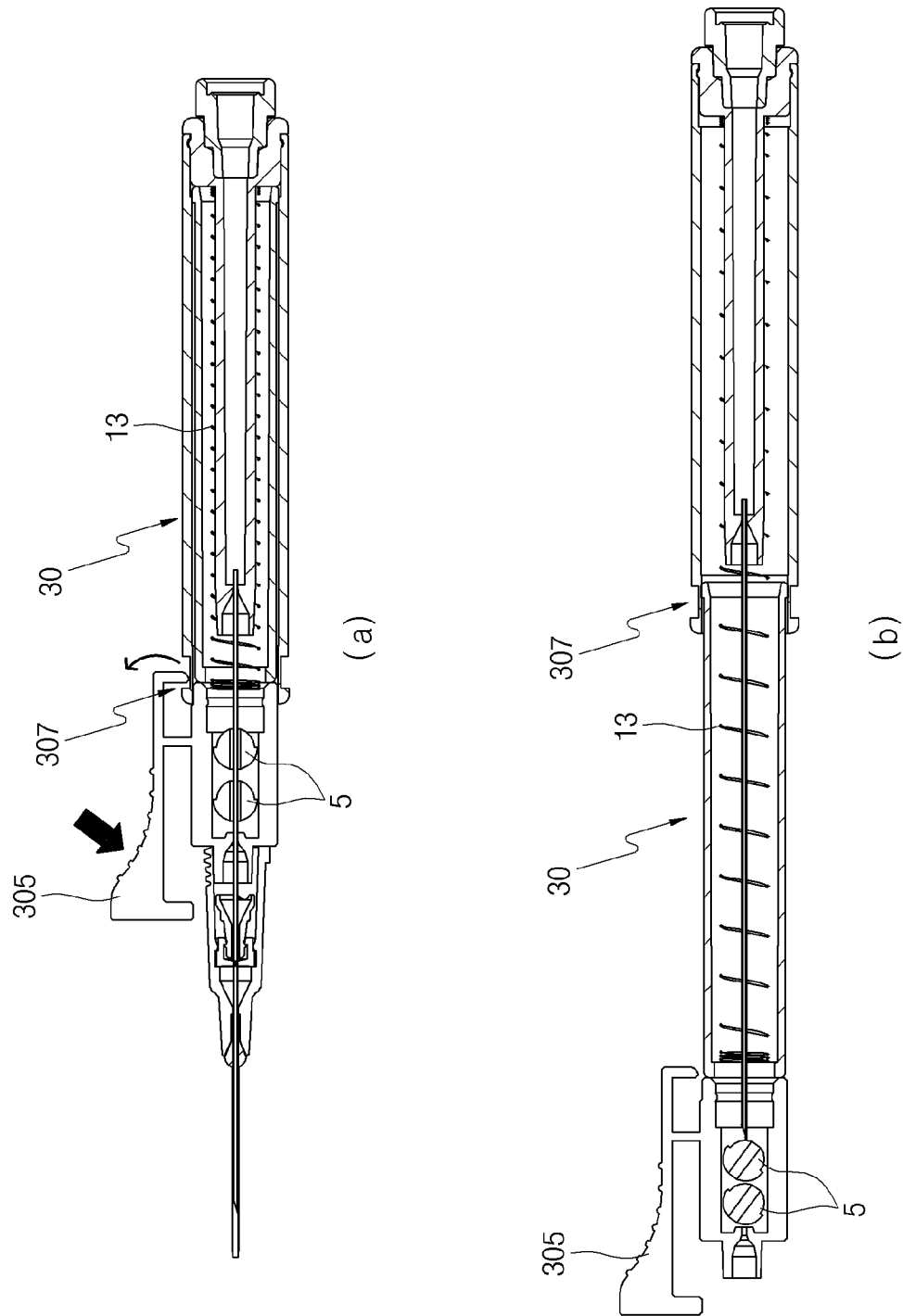
FIG. 11 shows an operation mechanism of the reuse prevention safety catheter according to the embodiment of FIG. 10.

FIG. 11 shows the operation mechanism of the reuse prevention safety catheter 1 according to the embodiment of FIG. 10. With reference to (a) of FIG. 11, when a user presses and pushes the holder 305 to a front side, a coupling state between the rear coupling part 307 of the holder 305 and the slide casing 30 is released. Accordingly, with reference to (b) of FIG. 11, the elastic force of the spring 13 disposed in the cannula plug 10 presses the slide casing 30 to the front side. Accordingly, a user's initial operation of operating the holder 305 is simple and then, due to the initial operation, the cannula plug 10 may be separated from the catheter hub 70 together with the elastic force of the spring 13. At the same time, the spring 13 sufficiently slides the slide casing 30, such that the internal needle 110 is surely separated from the locking guide unit 5. When the internal needle 110 is surely separated from the locking guide unit 5, the through-hole of the locking guide unit 5 is deformed, such that it is prevented that the internal needle 110 moves forward again.

INDUSTRIAL APPLICABILITY

The present disclosure provides a reuse prevention safety catheter which is produced by using the minimum number of injection molded parts and is structurally impossible to be manipulated by a user for reuse. The present disclosure guarantees low manufacturing costs and improved assemblability, and has a structural feature that a user cannot artificially place a needle at a position capable of being reused. Accordingly, a medical accident is prevented by preventing reuse of a disposable catheter and, when being discarded, the used catheter is discarded after an acute needle end is safely covered.

The invention claimed is:

1. A reuse prevention safety catheter, the catheter comprising:
a catheter hub having an external needle disposed on the catheter hub;
a cannula plug having an internal needle insertable and penetrable into the catheter hub and disposed on the cannula plug to introduce the external needle into a blood vessel and to be separated from the catheter hub; and
a locking guide unit having a through-hole configured to allow the internal needle to pass through,
wherein the through-hole is deformed when the internal needle is withdrawn, such that re-penetration of the internal needle is blocked,
wherein the locking guide unit comprises a first locking guide and a second locking guide, each of the first locking guide and the second locking guide having a truncated conical shape with an eccentric center of gravity and configured such that when the internal needle is withdrawn from the through-hole, an inclination in the first locking guide and the second locking guide is generated within an angular range of greater than 0° and less than 90° by gravity to change a position of the through-hole,
wherein the first locking guide and the second locking guide each have a gradually decreasing diameter at respective ends of the first locking guide and the second locking guide, and
wherein the second locking guide is located distal to the first locking guide, and the first locking guide and the second locking guide are symmetrically disposed with the respective ends of the first locking guide and the second locking guide opposite each other so that when the internal needle is first withdrawn from the second locking guide, the end of the second locking guide is lowered so that a symmetrical disposition becomes a staggered disposition and a path of the through-hole is changed.

2. The catheter of claim 1, further comprising:
a slide casing configured to be extended from the cannula plug to cover the internal needle,
wherein the locking guide unit is disposed at a front end part of the slide casing.

3. The catheter of claim 2, wherein the slide casing comprises a holder configured to be hooked by a finger to enable a user to separate the cannula plug from the catheter hub, wherein the locking guide unit is disposed in the holder.

4. The catheter of claim 1, further comprising:
a blood blocking unit disposed in the catheter hub to block backflow of blood.

5. The catheter of claim 1, wherein the locking guide unit is an injection-molded part independent of the cannula plug and maintains a locked state in the cannula plug by the internal needle, wherein when a locking force is removed as the internal needle is withdrawn, the inclination is generated in the locking guide unit, such that the position of the through-hole is changed.

6. The catheter of claim 1,
wherein a locking force of the first locking guide and the second locking guide is removed when the internal needle is withdrawn, such that the inclination is generated in the first locking guide and the second locking guide, respectively, and a longitudinal hollow path formed by the through-hole of the locking guide unit is collapsed by misalignment of the first locking guide and the second locking guide.

7. The catheter of claim 1, further comprising:
a spring providing elastic force pushing the cannula plug from the catheter hub,
wherein the spring pushes the cannula plug from the catheter hub to completely extend the internal needle from the locking guide unit.

* * * * *